United States Patent [19]
Gazdzinski

[11] Patent Number: 6,144,032
[45] Date of Patent: Nov. 7, 2000

[54] METHOD AND APPARATUS FOR MEASURING THE CONDITION OF DEGRADABLE COMPONENTS

[76] Inventor: Robert F. Gazdzinski, San Diego, Calif.

[21] Appl. No.: 09/074,207

[22] Filed: May 7, 1998

[51] Int. Cl.⁷ ................................................. G01N 23/222
[52] U.S. Cl. ...................................... 250/358.1; 250/269.6
[58] Field of Search ............................ 250/358.1, 390.04, 250/390.06, 390.07, 269.6, 390.01

[56] References Cited

U.S. PATENT DOCUMENTS

| | | | |
|---|---|---|---|
| 3,780,303 | 12/1973 | Smith, Jr. et al. ...................... | 250/301 |
| 4,209,695 | 6/1980 | Arnold et al. . | |
| 4,278,885 | 7/1981 | von Alfthan et al. . | |
| 4,317,993 | 3/1982 | Hertzog et al. . | |
| 4,365,154 | 12/1982 | Arnold et al. . | |
| 4,387,302 | 6/1983 | Givens . | |
| 4,499,380 | 2/1985 | Aggour et al. . | |
| 4,851,687 | 7/1989 | Ettinger et al. . | |
| 5,021,664 | 6/1991 | Hinshaw . | |
| 5,068,532 | 11/1991 | Wormald et al. . | |
| 5,076,993 | 12/1991 | Sawa et al. . | |
| 5,098,640 | 3/1992 | Gozani et al. . | |
| 5,239,568 | 8/1993 | Grenier . | |

*Primary Examiner*—Constantine Hannaher
*Assistant Examiner*—Albert Gagliardi
*Attorney, Agent, or Firm*—Gazdzinski & Associates

[57] ABSTRACT

An apparatus and method for the in-situ measurement of the condition of degradable components such as electrical cable insulation, valve internals, and gaskets. A stream of energetic subatomic particles is directed to the component under test, thereby inducing the emission of secondary gamma radiation which is detected by one or more radiation detectors positioned in proximity to the component. The secondary radiation emission spectrum is recorded and analyzed to identify features and/or changes resulting from the application of one or more stressors to the component. In the specific case of aging, the radiation spectra taken from the same component at different intervals during its lifetime are compared to identify changes in the component which then may be correlated with artificially (or naturally) aged specimens to estimate the relative level of aging of the component.

8 Claims, 13 Drawing Sheets

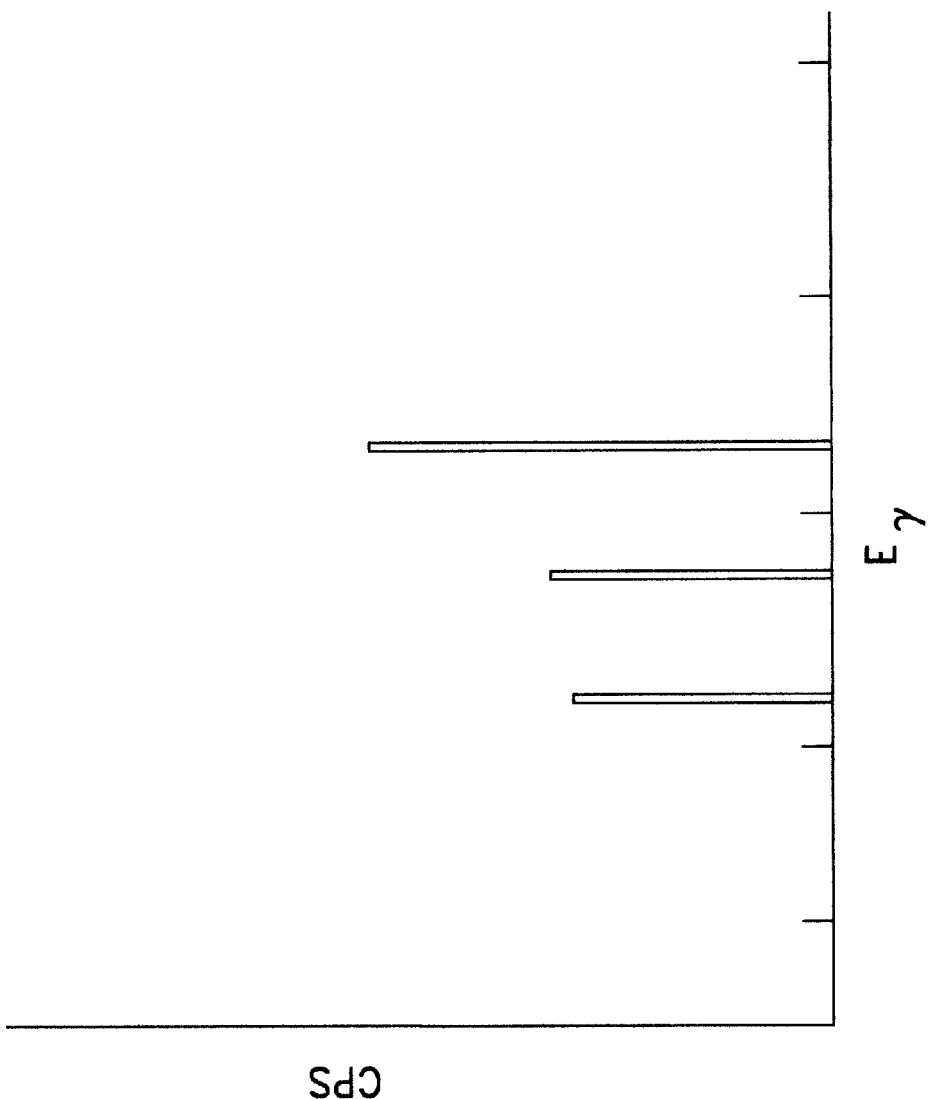

METHOD AND APPARATUS FOR MEASURING THE CONDITION OF DEGRADABLE COMPONENTS

BACKGROUND OF THE INVENTION

1. Field of the Invention

The present invention relates to the field of material aging research and management, specifically to the in-situ monitoring and estimation of the condition of various degradable components used in a wide variety of applications (including, inter alia, electrical cable, process system valves, aircraft, spacecraft, and automobiles) via neutron activation techniques.

2. Description of Related Technology

The aging of degradable components (particularly those constructed in whole or in part of organic compounds such as polymers) is of great importance to modem society. Such degradable components comprise a significant fraction of what may be termed as "critical" components in use in many industrial, aerospace, and automotive applications, both commercial and military. Included in this category are components such as electrical cable insulation, valve internals, bushings, seals, and gaskets. Degradation and ultimate failure of these so-called critical components is of paramount importance in that such failures may result in the unanticipated maintenance costs, loss of operational capability and availability, and even loss of human life.

Several different approaches to managing the aging of such components exist. One approach involves 1) subjecting laboratory or in-situ specimens of a given component to a progressive regimen of aging stressors such as heat, radiation, electrical potential, chemicals, and/or oxygen present in the anticipated operating environment (known generally as "artificial aging"); 2) identifying a critical parameter of the component's function in the desired application (such as dielectric strength for an insulator); 3) determining a maximum or minimum acceptable value for the chosen parameter; 4) correlating the maximum or minimum acceptable value to a given installed lifetime (for example, via aging models such as the Arrhenius equation); and 5) removing the component from service when the installed lifetime is reached. Note, however, that this approach has the distinct disadvantage of not directly monitoring the condition of a given component, thereby introducing potentially significant variations in component condition across various applications. Specifically, some applications may have aged more or less than expected (due to a variety of factors such as radiant heat or radiation shielding, variations in oxygen/inert gas concentration, aging prior to installation, inaccuracies in the aging model used, etc.), and hence are being replaced either prematurely or too late. More effective condition monitoring programs will utilize a similar approach as that outlined above, yet instead of rotely replacing a component at a given point in life, will monitor the degradation of the component as a function of time to determine it's rate of aging as compared to the artificially (or naturally) aged specimen. The primary drawbacks of these latter condition monitoring programs include the costs of monitoring, component inaccessibility, and component/device downtime. For example, the condition monitoring of a fluoropolymer valve seat requires either remote inspection or disassembly of the valve, thereby removing the valve from service for a period of time. In such cases, simple periodic replacement of the component during other scheduled maintenance may be more cost effective. In some instances (such as electrical cable, described further below), no periodic maintenance or replacement is ever scheduled; hence condition monitoring of some sort is almost a necessity. The enormity of cost associated with replacement of cable in, for example, a commercial nuclear power facility, underscores the need for effective aging assessment and monitoring techniques.

Electrical Cable

As previously indicated, the aging and unanticipated failure of power, control, instrumentation, and data transmission cable may have significant adverse effects on plant operation and maintenance (O&M) costs and downtime. Electrical and optical cables have traditionally been considered long-lived components which merit little in the way of preventive maintenance or condition monitoring due to their generally high level of reliability and simplicity of construction. Like all other components, however, such cables age as the result of operational and environmental stressors. Aging effects may be spatially generalized (i.e., affecting most or all portions of a given cable equally, such as for a cable located completely within a single room of uniform temperature), or localized (i.e., affecting only very limited portions of a cable, such as in the case of a cable routed near a highly localized heat source). The severity of these aging effects depends on several factors including the severity of the stressor, the materials of construction and design of the cable, and the ambient environment surrounding the cable. Detailed discussions of electrical cable aging may be found in a number of publications including SAND96-0344 "Aging Management Guideline for Commercial Nuclear Power Plants—Electrical Cable and Terminations" prepared by Sandia National Laboratories/U.S. Department of Energy, September 1996. Discussions regarding optical cable aging may be found, inter alia, in Electric Power Research Institute (EPRI) publications and telecommunications industry literature. The following description will be limited to electrical cable, although it can be appreciated that the principles of aging and analysis described herein may also be largely applicable to optical cabling as well as many other types of polymeric components.

Electrical cables come in a wide variety of voltage ranges and configurations, depending on their anticipated uses. Existing prior art low- and medium-voltage power and control cables such as that shown in FIGS. 1$a$–1$d$ are typically constructed using a polymer or rubber dielectric insulation 200 which is applied over a multi-strand copper or aluminum conductor 202. The insulation is often overlaid with a protective polymer jacket 204. In multi-conductor cables (such as those used in three-phase alternating current systems, as shown in FIGS. 1$a$ and 1$b$), a plurality of these individually insulated conductors are encased within a protective outer jacket 206 along with other components such as filler 208 and drain wires (not shown). These other components fulfill a variety of functions including imparting mechanical stability and rigidity to the cable, shielding against electromagnetic interference, and allowing for the dissipation of accumulated electrostatic charge. This general arrangement is used for its relatively low cost, ease of handling and installation, comparatively small physical dimensions, and protection against environmental stressors.

Current methods of evaluating electrical cable component aging generally may be categorized as electrical, physical, and microphysical. Electrical techniques involve the measurement of one or more electrical parameters relating to the operation of the cable, such as the breakdown voltage, power factor, capacitance, or electrical resistance of the dielectric. These methods have to the present been considered largely ineffective or impractical, in that they either do not show a good correlation between the parameter being measured and the aging of the dielectric, or are difficult to implement under normal operations. Furthermore, such techniques are often deleterious to the longevity of the insulation, and have difficulty determining localized aging within a given conductor.

Physical techniques including the measurement of compressive modulus, torsional modulus, or rigidity under bending often show a better correlation between the aging of the cable and the measured parameter (especially for low-voltage cable), and are more practical to apply during operational conditions. However, they generally suffer from a lack of access to the most critical elements of the cable, the individual electrical conductors and their insulation. For example, the measurement of compressive modulus by way of instruments such as the Indenter Polymer Aging Monitor are effective primarily with respect to the outer, accessible surface of the cable such as its outer jacket. Although correlations of the aging of the outer jacket to that of the underlying conductors have been attempted, these correlations are generally quite imprecise and are subject to a large degree of variability based on the specific configuration of the cable being tested (i.e., its materials of construction, insulation/jacket thickness, etc.), the presence of ohmically induced heating, shielding of the conductors against stressors by the outer jacket, and differences in the oxygen concentration at the conductor insulation versus that at the outer jacket. See EPRI TR-104075, "Evaluation of Cable Polymer Aging Through Indenter Testing of In-Plant and Laboratory Aged Specimens," prepared by the Electric Power Research Institute, January, 1996 for a discussion of the correlation between outer jacket and conductor physical measurements.

Other physical techniques such as the measurement of the tensile strength or elongation-at-break of the insulation material are inherently destructive and require a specimen of the aged cable for testing.

Another potential drawback to many of the physical techniques described above is disturbance of the bulk cable run during testing. In some applications, the dielectric of the cable being evaluated may be highly aged and embrittled, yet still completely functional. However, substantial movement of the cable (such as picking the cable up and clamping on a test device) may produce localized elongation stresses beyond those corresponding to the elongation-at-break for the insulation and/or jacket material, thereby inducing unwanted cracking of the insulation and/or jacketing and potential electrical failure.

Microphysical techniques such as the measurement of insulation oxidation induction time (OIT), density, gel or plasticizer content, infrared absorption spectroscopy, UV spectroscopy, and NMR are generally quite accurate, yet require samples of the cable insulation and/or jacket for analysis. For jacketed conductors, such samples are generally only available at the ends of the cable where the conductors are terminated to a source or load, and not anywhere between. Furthermore, as with the physical techniques described above, the results of any such testing are necessarily applicable only to the localized area of the cable from which the specimen was taken, which may or may not be representative of the rest of the cable. Hence, one can either take a small sample of material from the outer jacket of the cable and attempt to extrapolate the results of the aging analysis to the underlying conductors, or alternatively take a sample at the ends of the conductor itself near its terminations and extrapolate these results to the rest of the unexposed conductor. Under either alternative, a substantial degree of uncertainty and imprecision exists. Plant operators are also generally reticent to allowing the removal of even small samples of material from their cables, especially in applications where plant safety and continuity of electrical power are critical.

Another common problem in applying either physical or microphysical techniques to a localized portion of cable is the existence of conduit. In the typical power or industrial plant, many miles of cable may be encased within metallic or plastic conduit, thereby rendering it all but inaccessible. While it is true that such conduit also affords the cable additional protection from most stressors (such as heat and radiation), it also may preclude any effective estimation of aging using existing techniques. For example, the aging of a portion of nuclear plant safety-related cable contained in a conduit running directly over a large radiant heat source may be for all intents and purposes immeasurable during it's installed lifetime. While the remainder of the cable not in direct proximity to the heat source may be largely unaffected, the insulation of the cable in the region directly adjacent to the heat source may undergo dramatically accelerated aging and ultimately failure well in advance of the rest of the cable.

Fast Neutron Activation

The technique of fast neutron activation (FNA) is well known in the nuclear arts. Generally speaking, this technique employs a stream of energetic (fast) neutrons to induce secondary gamma ray emission from a target object via inelastic scattering with nuclei in the target. The gamma ray spectrum associated with a given element is unique and identifiable given sufficient energy resolution. Heretofore, FNA systems have been used exclusively in the detection and identification analysis of organic materials in obstructed locations (such as in contraband detection or bore hole exploration; see for example U.S. Pat. No. 5,098,640, "Apparatus and Method for Detecting Contraband using Fast Neutron Activation"). Such techniques, however, have not been applied to the in-situ analysis of changes in the atomic structure of a material resulting from the application of stressors (such as heat, nuclear radiation, oxygen/ozone, etc.). Furthermore, existing neutron scanning and detection systems necessarily utilize very high neutron fluxes (>1E10 n/s-4 $\pi$) in order to minimize analysis time. Such systems can induce significant damage to both inorganic (such as metals) and organic materials. While neutron radiation primarily results in atomic displacement effects (which are highly detrimental to inorganics), it also induces a substantial degree of ionization within organic materials.

Based on the foregoing, it would be most desirable to provide an apparatus and method which allows an operator to more accurately assess the aging an in-situ degradable component in a substantially non-destructive manner and without requiring direct access to the component. Such apparatus and method could, for example, be used to estimate the aging of an electrical cable within a metallic conduit, or similarly to estimate the aging of a valve internal component while still installed within its host valve.

SUMMARY OF THE INVENTION

The present invention satisfies the aforementioned needs by providing an improved apparatus and method for the in-situ estimation of polymeric component degradation and aging.

In a first aspect of the invention, a collimated stream of energetic ("fast") neutrons generated by a neutron source is used to bombard the subject in-situ degradable component in order to induce inelastic scattering with various constituent atoms in the materials of construction. Such inelastic scattering results in the production of gamma rays of varying energy (the energy being dependent in part on the identity of the scattering atom). One or more gamma ray detectors are placed in proximity to the irradiated component to measure the resulting gamma ray spectra during bombardment. Since the relative concentrations of various constituent atoms within certain component material(s) change as a function of aging, the gamma emission spectra from the component will also change with aging. Scattering resulting from neutron interaction with metal atoms or other essentially aging-independent materials (such as those in the conductor, shield, or conduit of an electrical cable, for example) will remain effectively constant, and therefore is easily differentiable from scattering associated with age-variant atomic concentrations such as plasticizers or fire retardants present in the polymers.

In a second aspect of the invention, an improved method for estimating the aging of a degradable component using the previously described apparatus is disclosed. Gamma emission spectra of an in-situ test component are taken at various times during its installed lifetime, and compared to each other as well as other spectra obtained from laboratoryaged specimens of similar components. In one embodiment, the analog gamma emission spectrum is converted to a digital representation using an analog-to-digital converter (ADC), electronically filtered, and then subtracted from prior spectra to generate "difference" spectra for the component under test. Such difference spectra are compared to those derived from known aged specimens, and may further be analyzed and compiled to generate a statistical model of aging within a given type of component. In this fashion, the relative level of aging of the in-situ component can be reliably estimated at any given point during its lifetime.

BRIEF DESCRIPTION OF THE DRAWINGS

FIG. 8 illustrates a typical difference spectrum generated by differencing the gamma emission spectra of FIGS. 6a and 6b.

DETAILED DESCRIPTION OF THE PREFERRED EMBODIMENTS

Reference is now made to the drawings wherein like numerals refer to like parts throughout.

While the following description is made primarily with reference to electrical cable, it can be appreciated that many of the aspects of the present invention may generally be adapted to use on other types of components and devices including, without limitation, optical cable, valve internals, and automotive or aircraft engine components such as gaskets or seals. Furthermore, analyzed components need not necessarily be polymeric in composition, but rather may be comprised of any material whose gamma emission spectrum varies measurably as a function of the aging of (or other stressors applied to) the material. Finally, while the use of neutrons and gamma rays are described in detail, the use of other forms of radiation (both incident and secondary) for component degradation evaluation is contemplated by the invention.

Figure 1A:
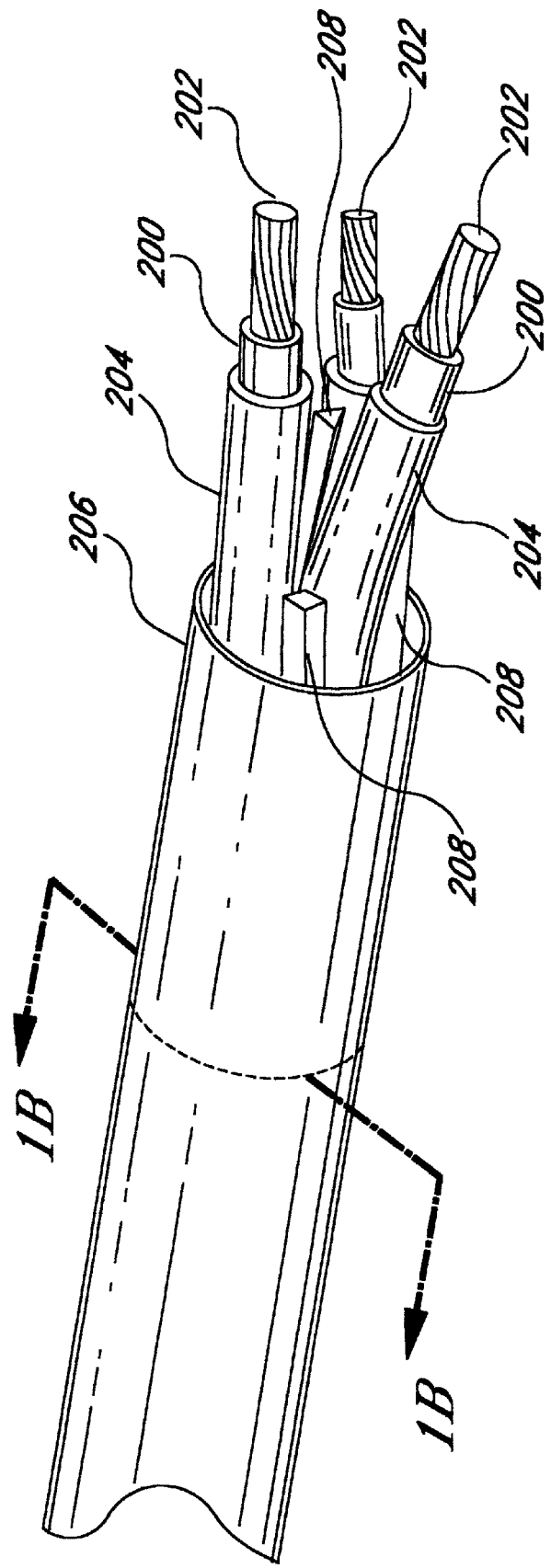
FIGS. 1a–1d are perspective and cross-sectional views of two typical prior art electrical cables (3 φ ac and 2-conductor dc, respectively), showing the cable conductors, insulation, shielding, and jacket.
Figure 1B:
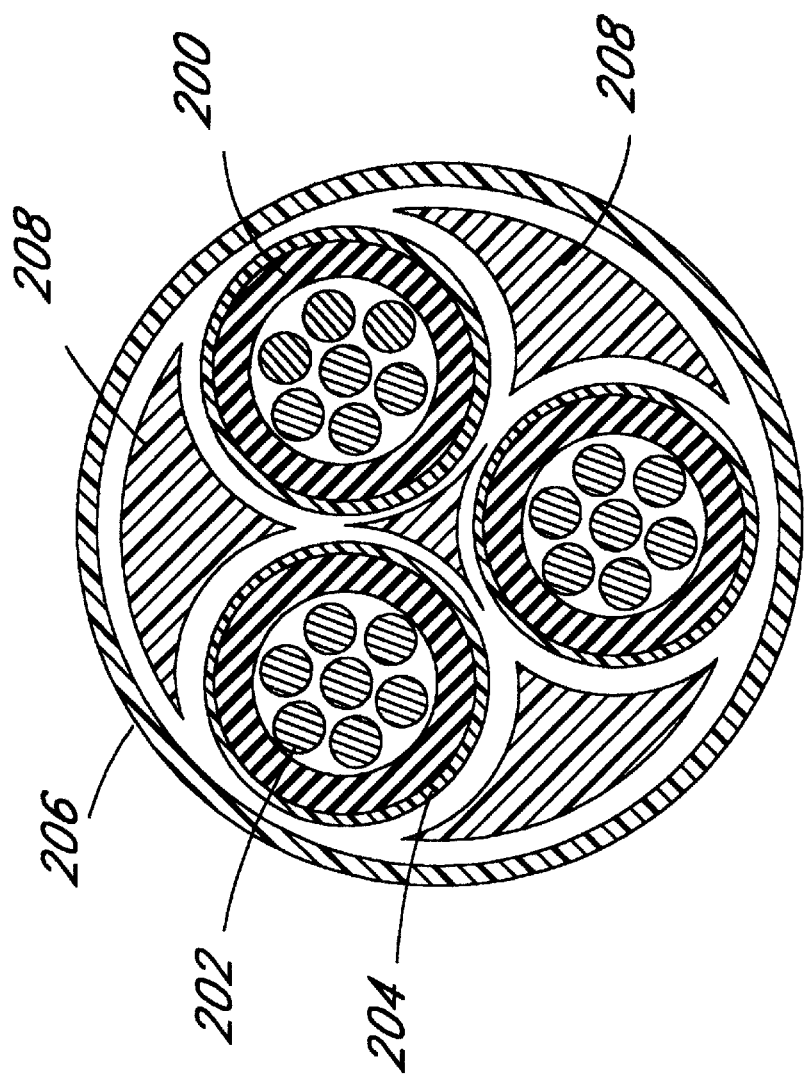
Figure 1C:
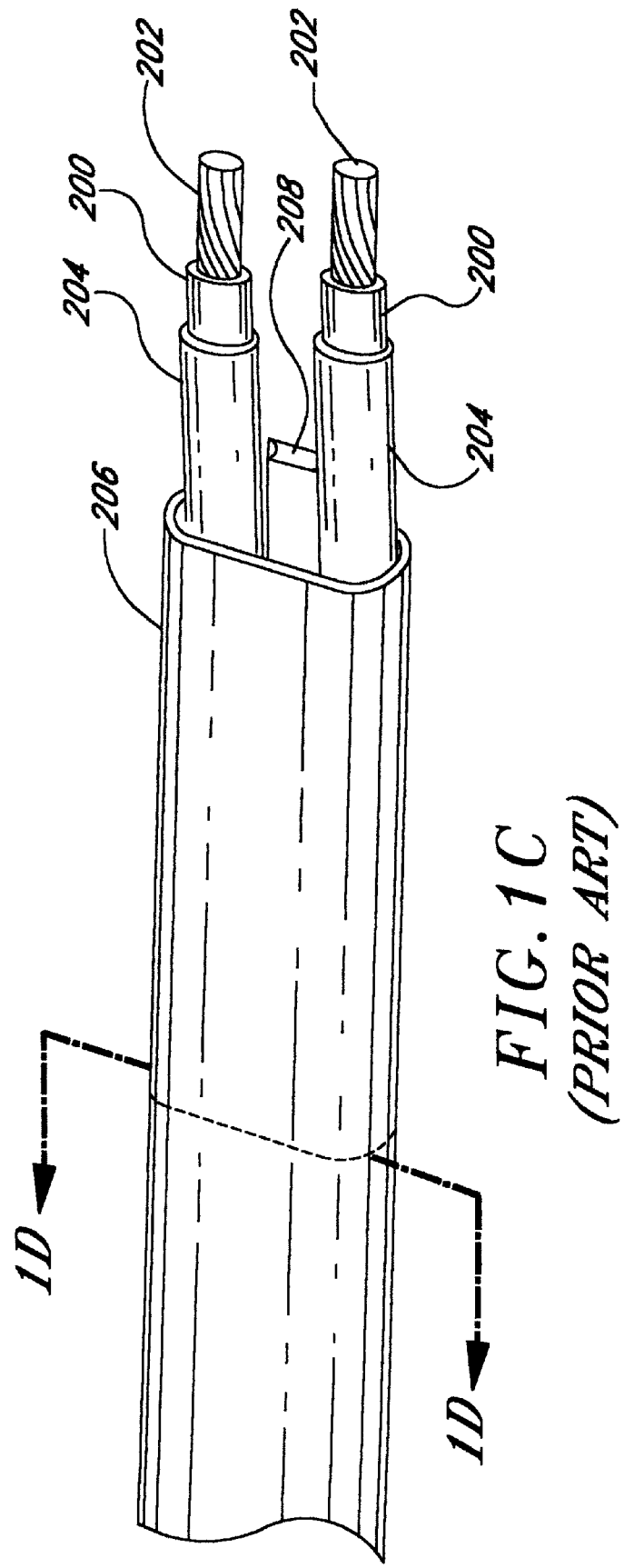
Figure 1D:
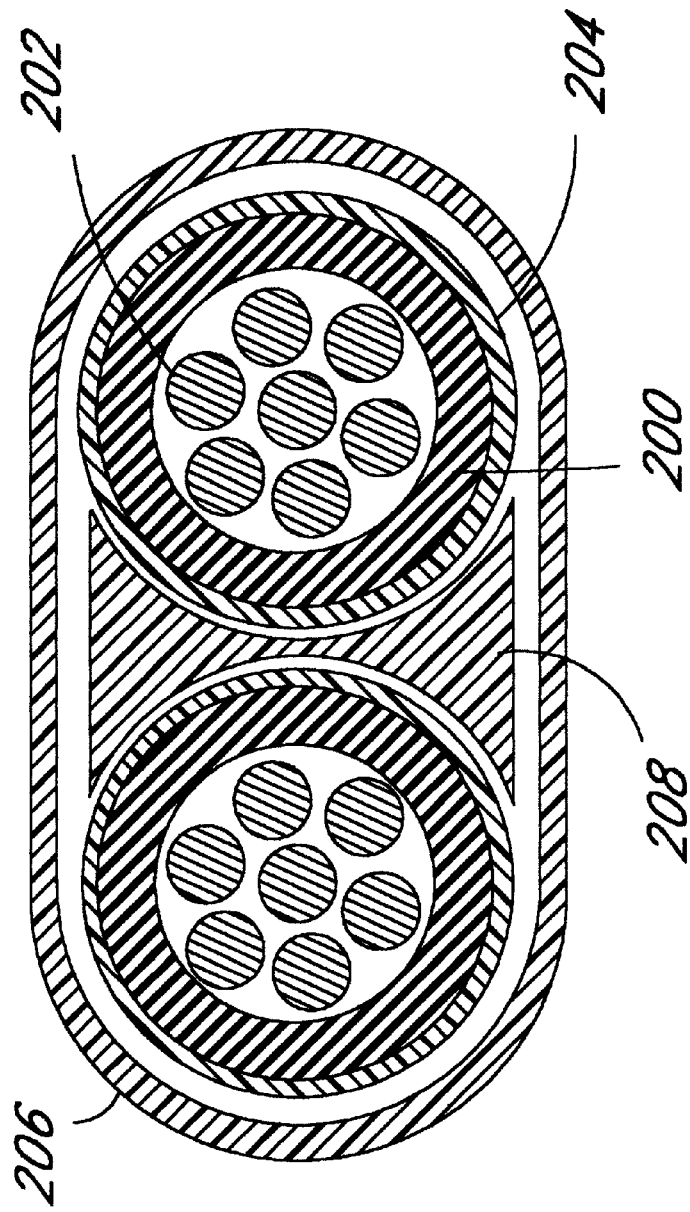
Figure 2:
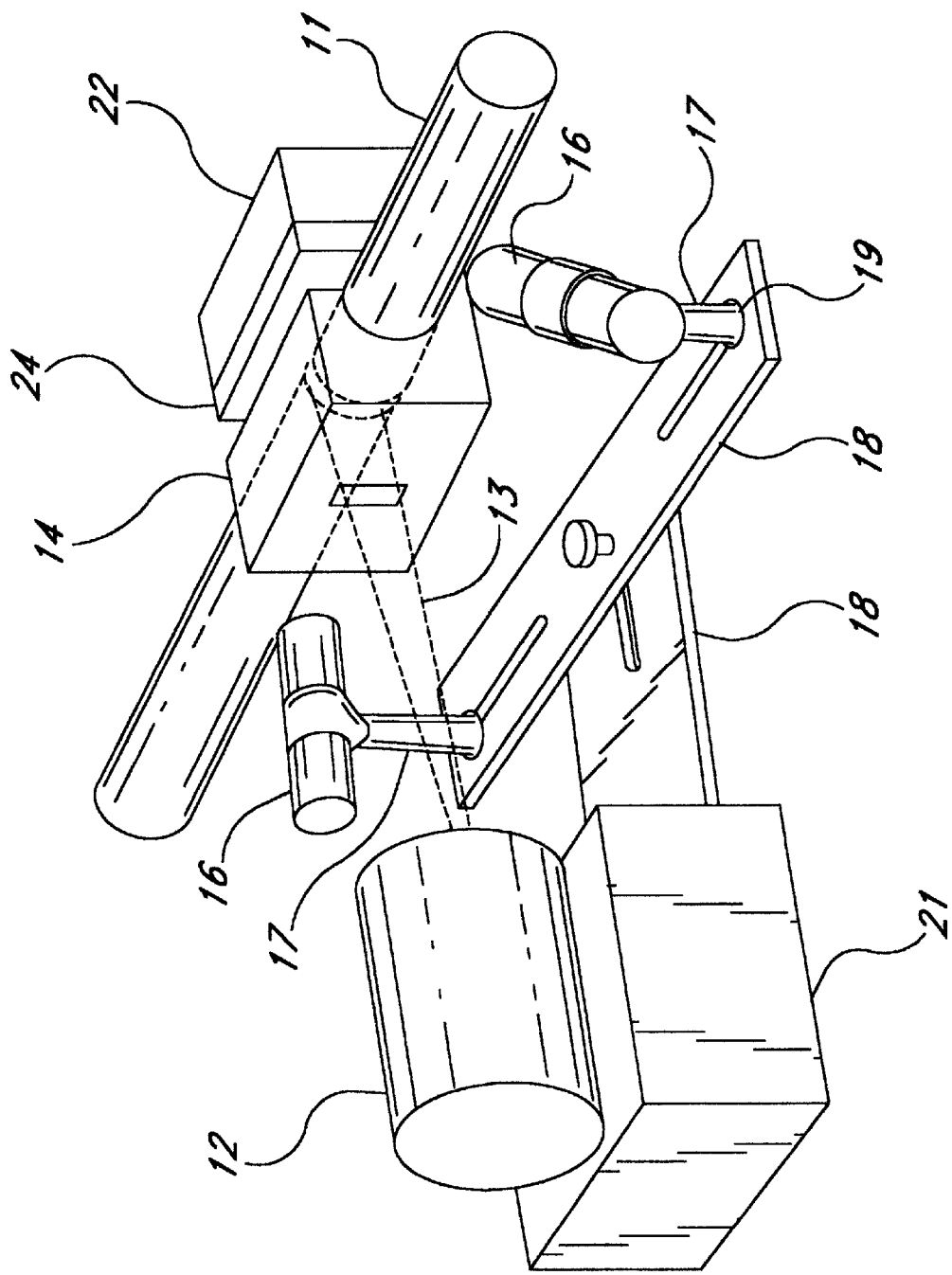
FIG. 2 is a perspective view of a first embodiment of the condition monitoring apparatus of the present invention.

FIG. 2 shows a first embodiment of the improved condition monitoring apparatus 10 of the present invention. A neutron source 12 is positioned generally in relative proximity to the subject 11 being evaluated, in the present case an electrical cable installed within a conduit (see FIG. 1). The source 12 may be of any readily available type which produces sufficiently energetic (i.e., typically between 5 and 15 MeV) neutrons in quantities necessary to generate the desired net neutron flux 13 after collimation (described further below). A Kaman Nuclear particle generator utilizing a deuteron/tritium beam having 14 MeV neutrons is used as the source 12 in this embodiment, although it can be appreciated that other types of sources (such as those employing a deuterium/deuterium, deuterium/beryllium, or hydrogen/lithium beam) may be used with equal success. Furthermore, although the neutron source 12 of the present embodiment is continuous in nature, pulsed sources may also be employed, depending on the needs of the intended application. Pulsed fast neutron sources and systems are well known and understood in the art; see for example, U.S. Pat. No. 5,076,993, "Contraband Detection System Using Direct Imaging Pulsed Fast Neutrons."

In the present embodiment, fast neutrons having energies on the order of 14 MeV are utilized, although neutron energies outside this range may also be used depending on the specific application. For example, thermal neutrons (<<1 MeV) may be particularly useful for the detection of certain atoms such as nitrogen. The present invention contemplates the use of either fast or thermal neutrons, or both. Note that within a certain range of neutron energies, 1) the production of gamma rays at certain energies is significantly enhanced in certain materials, and 2) the energy of gamma rays resulting from neutron scattering are essentially constant. A practical consequence of varying neutron energy is the change in probability of creation of a given gamma event. Neutron flux is also a determinant of gamma ray production; higher incident neutron flux will, holding all else constant, generally produce a higher gamma flux.

A desirable characteristic of the neutron source 12 is comparatively small size and relative portability to permit in-situ testing of components. However, since the scattering cross-section of energetic neutrons in air is quite low, the source may be placed somewhat remotely to the test subject if desired without appreciable reduction in efficiency. The source of the present embodiment is fitted with a collimator 14 on its outlet which spatially collimates the neutron beam 13 from the source 12 prior to reaching the test subject. The collimator 14 may constructed of any material which effectively attenuates energetic neutrons, such as polyethylene (formulated with or without additives such as boron) or lead. In the present embodiment, polyethylene is chosen due to its comparatively light weight, ease of manufacturing, low cost, and high neutron absorption/scatteringcross-section.

Figure 2A:
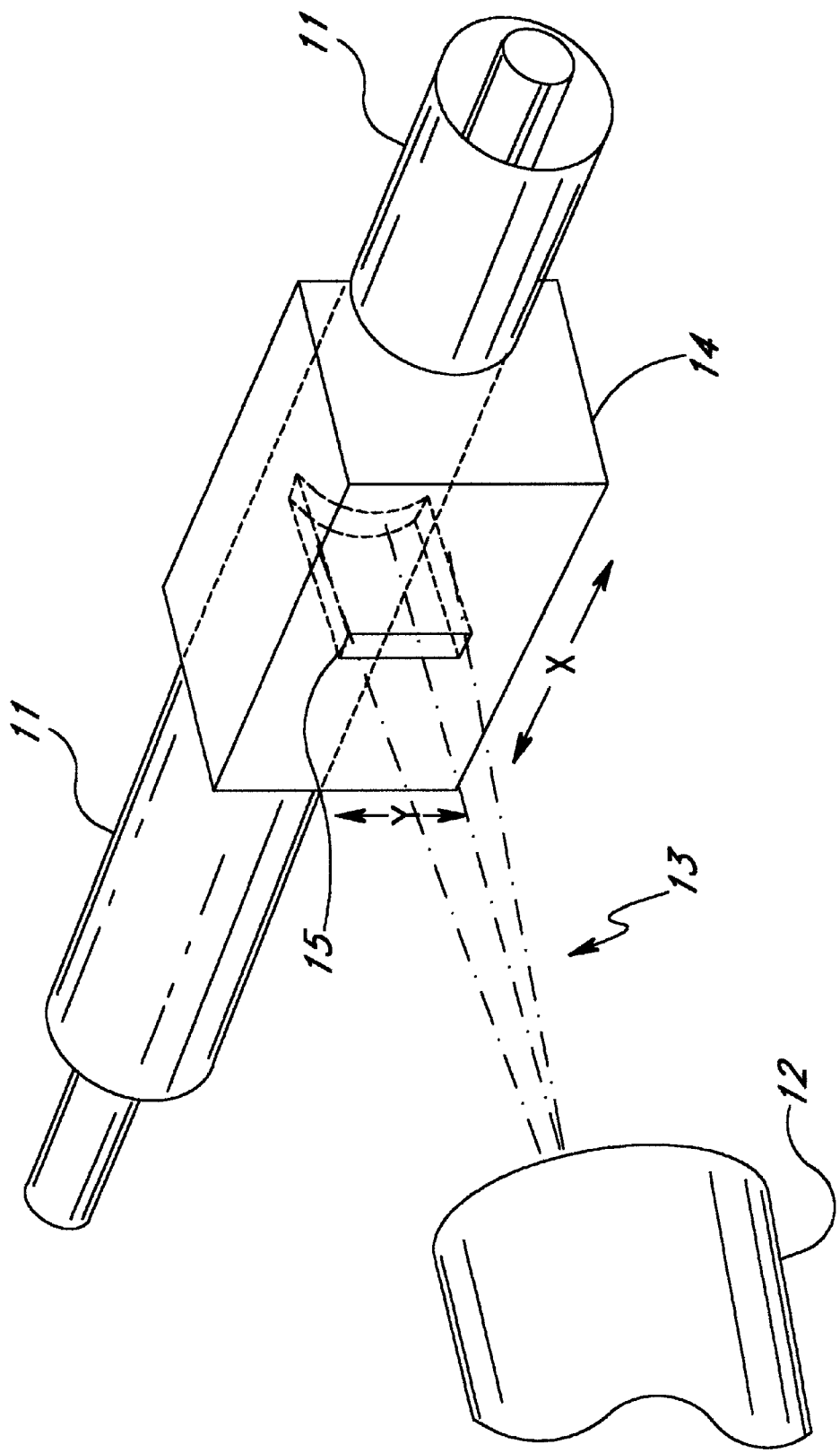
FIG. 2a is a perspective view of a first embodiment of the collimator of the condition monitoring apparatus of FIG. 2.

As shown in FIG. 2, the collimator 14 reduces the exposure of surrounding portions of the test subject to the neutron beam 13, and spatially refines the beam such that more precise testing of specific components can be performed. For example, as shown in FIG. 2a, the beam may be collimated disproportionately in the X and Y planes such that an exposure slit 15 is formed. In this fashion, a "slice" of a test subject 11 (electrical cable in this case) may be tested. Similar to techniques employed in prior art axial tomography, data from several of such slices may be electronically fused by the analyzer 60 to provide a spatial representation of the aging of the cable. Alternatively, the neutron beam 13 may be collimated to a tightly focused beam of essentially circular cross-section to allow examination of a very precise area within a structure (such as the stem seal of a valve).

Referring again to the embodiment of FIG. 2, one or more gamma ray detectors 16 are mounted on separate articulated arms 17 attached to a supporting frame element 18, the latter being which is moveable in relation to the source 12 and its pedestal 21. In this fashion, a broad range of detector positions relative to the source 12 can be achieved such that optimal test efficiency and adaptability can be supported. For example, the detector arms 17 may be positioned relative to the test subject 11 such that the maximum gamma event rate is achieved for a given neutron flux and energy. The frame element 18, detector arms 17, and articulated joint(s) 19 shown in FIG. 1 may be constructed in any number of well known and understood configurations, and fabricated using any suitable material such as steel, aluminum, or polymer.

The gamma detectors 16 of the present embodiment are neutron shielded high purity Germanium crystal detectors of the type well known in the art, the theory of operation of which is described in further detail below. Such detectors have the important advantage of high spectral resolution (typically less than 1%) as compared to other types of gamma detectors. It should be noted, however, that any type of gamma ray detector having sufficiently high spectral resolution may be used in the present invention.

In addition to the collimator 14, neutron shielding 22 and gamma ray shielding 24 is optionally utilized to shield the equipment operator, nearby personnel, and equipment from the relatively high neutron and gamma radiation fluxes generated by the apparatus 10. The primary object of the neutron and gamma shields is to allow testing of components in a typical setting or environment (such as a nuclear power plant) which may be populated during testing. In this fashion, elaborate precautions associated with high dose-rate/high energy radiation sources (such as those utilized during radiography) can be largely obviated. It should be noted however that while highly desirable, neutron and gamma shielding 22, 24 are not essential components of the present invention. For example, the equipment operator can be located remotely and areas adjacent to the test location evacuated as necessary to eliminate any potential hazards to personnel resulting from neutron/gamma exposure.

Figure 3:
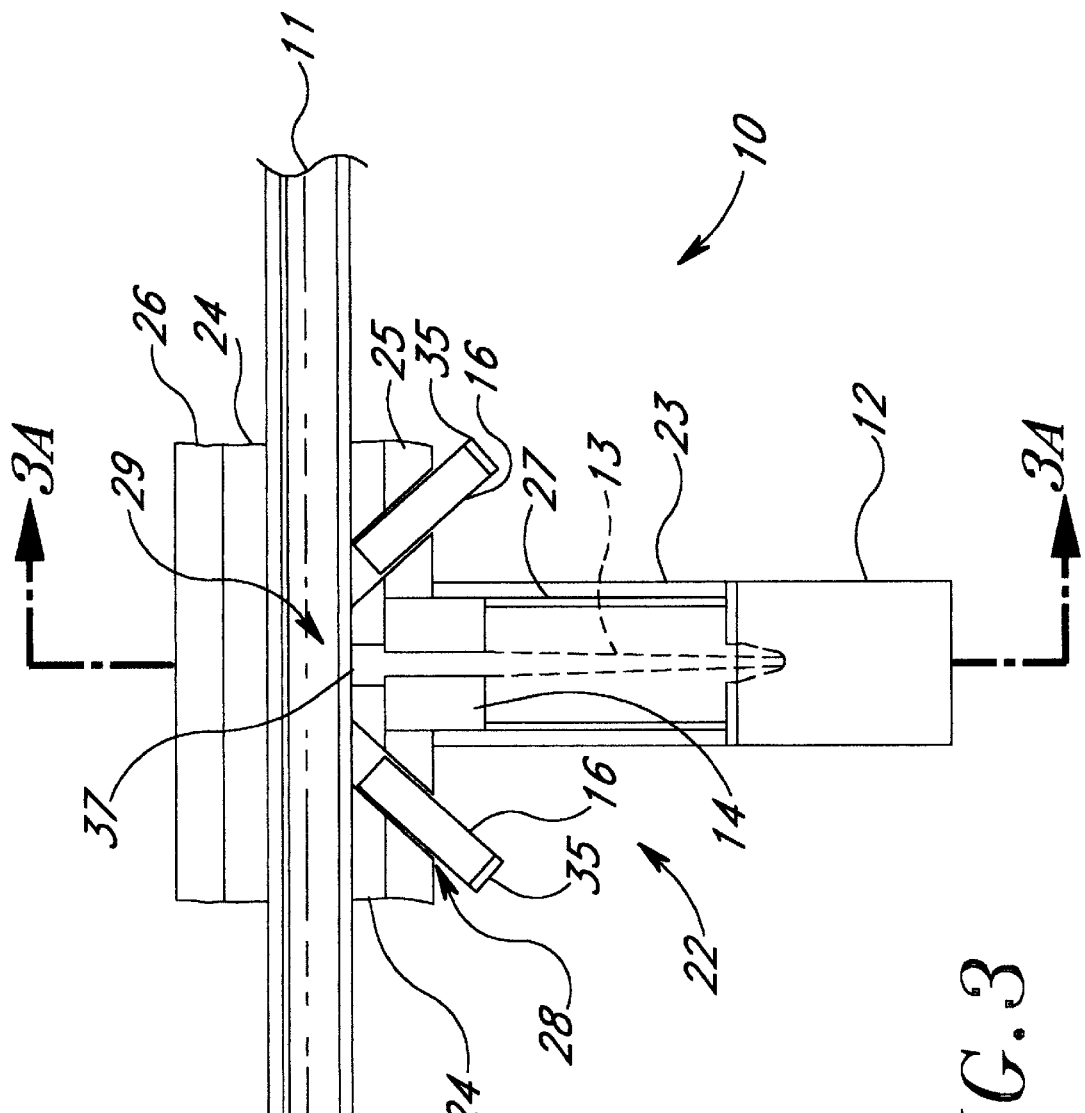
FIG. 3 is a top cross-sectional view of a second embodiment of the condition monitoring apparatus of the present invention.

A second embodiment of the condition monitoring apparatus of the present invention is shown in FIG. 3. The neutron shield 22 of this second embodiment is a two-piece device having 1) a hollowed cylinder 23 with shield extension element 25 attached thereto, the shield element 25 adapted to the test subject 11 shape (in the present case, a sectioned cylinder for use with an electrical cable conduit), and providing protection against backscattered or deflected neutrons; and 2) a backstop element 26 having a similarly adapted shape. The backstop element 26 is mounted to the shield element 25 via a hinge or similar device thereby permitting the rapid positioning of the apparatus 10 around the test subject 11. The material of construction neutron shielding 22 in the present embodiment is again chosen to be polyethylene, although it can be appreciated that other types of materials may be used. The shield element 25 and cylinder 23 also contain optional gamma shielding elements 27 to limit exposure of the neutron source 12, operator, and electronics to gamma exposure resulting from neutron irradiation. These gamma shield elements 27 are constructed of material similar to the main gamma shield 24 since the attenuation of MeV-energy gammas by polyethylene is generally poor.

As shown in FIG. 3, two gamma detectors 16 are mounted within recesses 32 within the neutron shield element 25 adjacent to the gamma shield 24. To minimize the size and weight of the gamma shield (which is appreciably more dense than the neutron shield 22), the gamma shield is placed within the neutron shield elements 25, 26, and penetrations 28 are cut into the gamma shield 24 to permit the maximum system count rate efficiency. The gamma shield 24 is comprised of a plurality of steel or lead interlocking components which effectively shield the majority of the solid angle (4 π) around the test subject 11. The gamma shield 24 also contains a neutron beam penetration 29 which allows passage of the neutron beam 13 from the source 12 to the test subject 11. Gamma "streaming" through the detectors and penetrations may be mitigated through the use of a lead blanket, if desired, or the detectors 16 each "capped" with a form fit element 35 as shown in FIG. 3. It can also be appreciated that while two detectors are shown in the present embodiment, any number of detectors may be utilized depending on the specific application.

Note that for both the neutron and gamma shields 22, 24, lateral radiation streaming (i.e., out the sides of the shields longitudinally along the cable 11) is minimized in part by the cable and conduit (if any). This is due largely to the construction of these components: the cable generally consists of a metallic conductor(s), with polymer insulation and jacketing, while the conduit is often metallic in construction (typically either aluminum or steel). Hence, as the neutron and gamma shields 22, 24 are made to extend laterally from the neutron beam impact point 37 on the cable 11, the amount of shielding provided by the cable and conduit is increased, since the effective gamma and neutron shielding thickness increases for all solid angles.

Figure 3A:
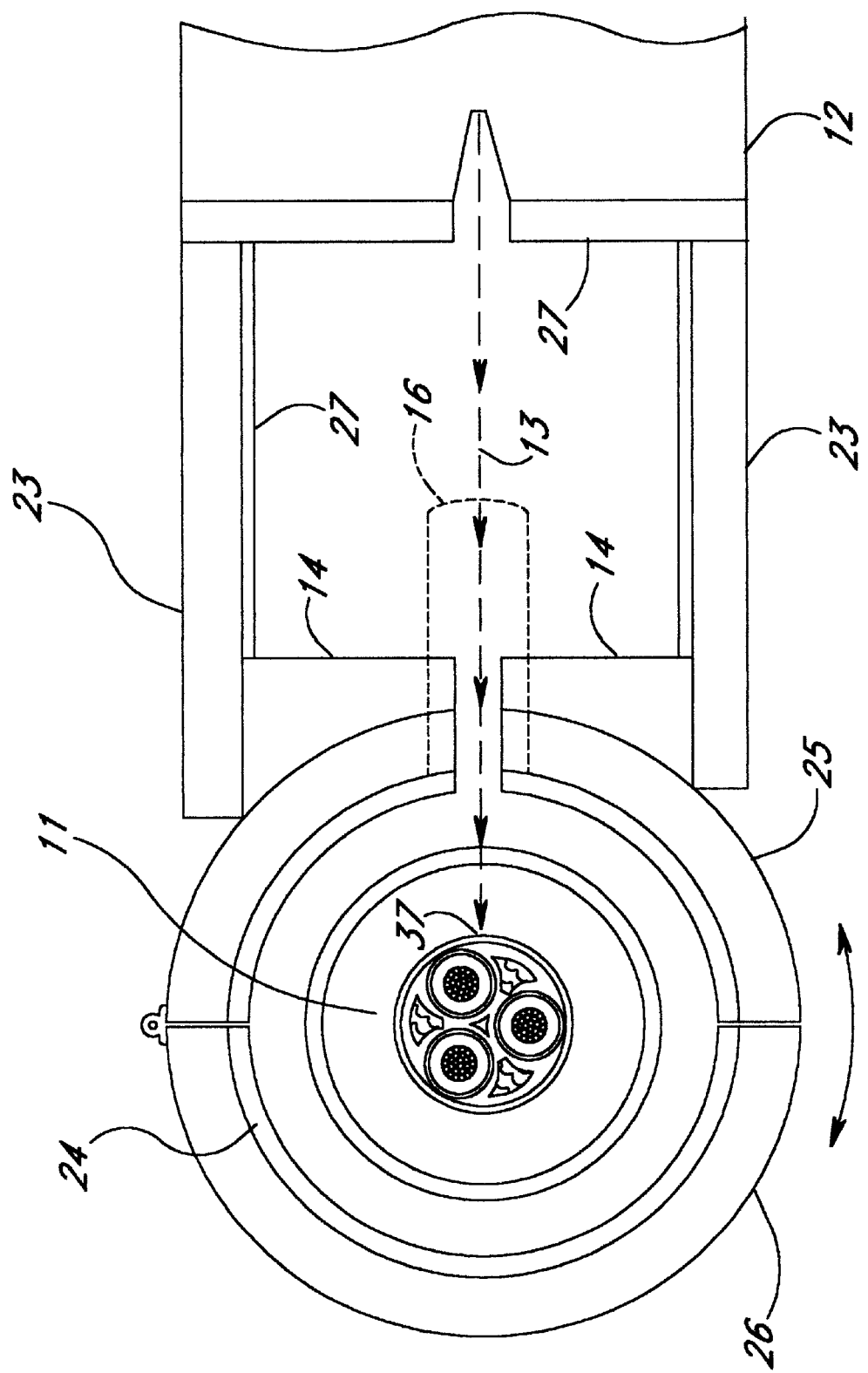
FIG. 3a is a side cross-sectional view of a second embodiment of the condition monitoring apparatus of the present invention, taken along line 3a—3a of FIG. 3.

FIG. 3a shows a cross-section of the system taken perpendicular to the longitudinal axis of the cable 11, illustrating the relative locations of the above-described components.

Gamma Ray Spectral Analyzer

Figure 4:
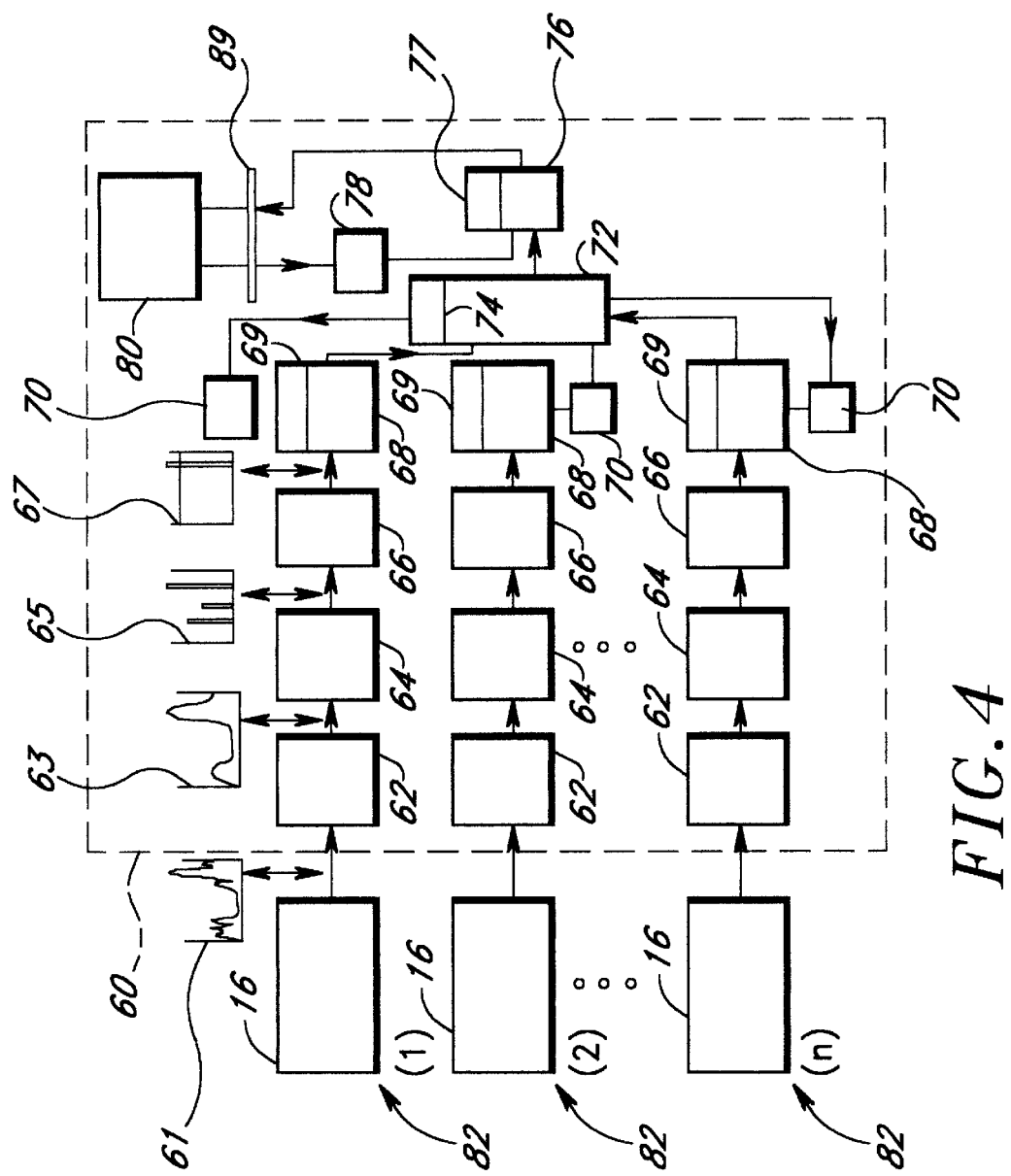
FIG. 4 is a schematic block diagram of a first embodiment of the analyzer of the present invention, showing the detector channels and signal processing equipment.

Referring now to FIG. 4, gamma rays detected by the gamma detectors 16 described above are processed by the system analyzer 60 in order to produce gamma energy spectra useful for the evaluation of component condition and aging. Generally, the analyzer consists of multiple detector channels having the following major components: 1) a pulse shaper 62; 2) an analog-to-digital converter (ADC) 64; 3) a pulse height discriminator 66; 4) a first stage FIFO buffer 68 and associated buffer manager 70; 6) a logic gate 72; 7) a local memory 74; 8) a second stage FIFO buffer 76 and associated buffer manager 78 and 9) a personal or laptop computer 80. The function and operation of each component is described below. Note that while one specific embodiment of analyzer 60 is described herein, any type and configuration of electronic signal analyzer which performs the desired functions (i.e., gamma ray spectral processing) may be used without departing from the spirit of the invention. For example, a conventional multi-channel analyzer (MCA) and nuclear scalers may be used with equal success.

As previously described, high purity crystalline scintillation detectors 16 are used for the detection of gamma rays in the present invention. In a scintillation detector, a gamma of a given energy excites crystal to produce lower energy quanta (lower frequency electromagnetic radiation). These lower energy quanta are subsequently detected by a photomultiplier (PM) tube, the output of which is an analog signal representing the detected gamma events. Specifically, the output of the PM tube is a series of analog pulses, each pulse corresponding to a gamma detection event and having an amplitude essentially proportional to the energy of the detected gamma.

Separate detector channels 82 (as opposed to a common or multiplexed arrangement) are utilized in the embodiment of FIG. 4 to, inter alia, allow single detector processing, increase the system efficiency, and allow coincident or near-coincident gamma detection events occurring within different detectors 16 to be counted by the circuitry. Note that coincidence circuitry for the detector channels 82 is not required in the present embodiment, since no neutron/alpha particle or neutron/gamma correlation is performed. However, utilization of such techniques (as well as neutron time-of-flight) for spatial resolution within the test subject 11 is contemplated by the present invention.

Referring again to FIG. 4, the present embodiment utilizes one or more pulse shapers 62 to shape the analog pulses received from each detector 16 as required. Shaping is often necessary to account for ballistic deficit and charge trapping, two effects associated with scintillation detectors well known in the art. While the specific origins of each of these phenomena are documented in a number of publications, their effects are of more significance to the present invention since they tend to distort the shape, timing, and amplitude of the pulses 61 produced by the photomultiplier circuitry in the detectors 16. Specifically, ballistic deficit tends to broaden and delay the pulse, whereas charge trapping tends to distort the amplitude of the pulse, thereby reducing spectral resolution. Many commercially available detectors incorporate pulse shaping circuitry to allow compensation for these effects. The pulse shaper(s) 62 of the present invention may be of any type (such as, for example, those employing pulse integration, or the "two pulse" method as disclosed in U.S. Pat. No. 5,021,664) which sufficiently mitigates the effects of ballistic deficit, charge trapping, or other similar phenomena. The signal output 63 from the pulse shaper(s) 62 merely must be such that a sufficiently high degree of spectral resolution can be obtained for purpose of discriminating gamma lines attributable to individual elements (described further below).

In order to take advantage of the great computational capability inherent in modern digital processors and integrated circuits, the analog pulses are converted to binary digital data 65 representative of gamma ray energy, as shown in FIG. 4. This conversion is accomplished in the present embodiment through a standard analog-to-digital converter (ADC) 64. For example, a standard 12-bit ADC, such as the TLC2500 series devices manufactured by Texas Instruments Corporation, will provide more than 4,000 possible "bins" ($2^{12}$ or 4096) for gamma energy resolution while also allowing for multiple analog inputs. Assuming a gamma energy range of 0–15 MeV, this allows for a spectral resolution of approximately 3.66 KeV. This level of energy resolution is more than adequate for the purposes of the present invention (considering the spectral resolution capability of the Germanium detectors), and the 12-bit ADC is compatible with a broad variety of commonly available FIFO buffers, logic gates, and other digital hardware as described further below.

After conversion to a multi-bit digital representation by the ADC 64, each pulse is passed through a digital pulse-height discriminator (PHD) 66. Pulse height discrimination is used to eliminate or screen ranges of the detected gamma spectrum which are of little or no analytical value. For example, the PHD 66 can screen all pulses below a given desired threshold energy 67. In this fashion, the processing burden on each detector channel, and computational burden on the logic gate 72 can be reduced. Alternatively, the PHD 66 can be selectively configured to pass all signals to the logic array such that a more complete spectrum can be analyzed. The PHD 66 can be embodied in any of a wide variety of hardware devices well know in the electronic arts, or may be conveniently implemented via the logic gate 72, as represented by the dashed lines between the PHD 66 and the logic gate 72 in FIG. 4.

Conceptually similar to pulse height discrimination described above, filtering in the context of the present invention relates to the filtering out of specific pulses having unwanted gamma ray energies, such as those associated with inelastic scattering of neutrons from elements invariant as a function of stressor application, those associated with intervening materials (such as aluminum or steel conduit), or those not associated with inelastic neutron scattering (such as background radiation). The binary digital format of each pulse after conversion by the ADC 64 is well suited to rapid discrimination and filtering by the logic gate 72, since the logic gate may be easily programmed to efficiently eliminate data stored in memory array addresses associated with unwanted discrete gamma energies. For example, if the gamma energies associated with the $400^{th}$ and $4000^{th}$ bins of the spectrum must be filtered, the logic gate can simply "skip over" these addresses when reading data out to the second stage buffer, as described further below. It should be noted that pulse height discrimination (as well as filtering) can be accomplished after the first stage buffer 68, using a similar approach. One possible detriment to this approach, however, is that the first stage buffers must then process and store data associated with all gamma energies as opposed to a greatly reduced set when pulse height discrimination is performed prior to the first stage.

Figure 5:
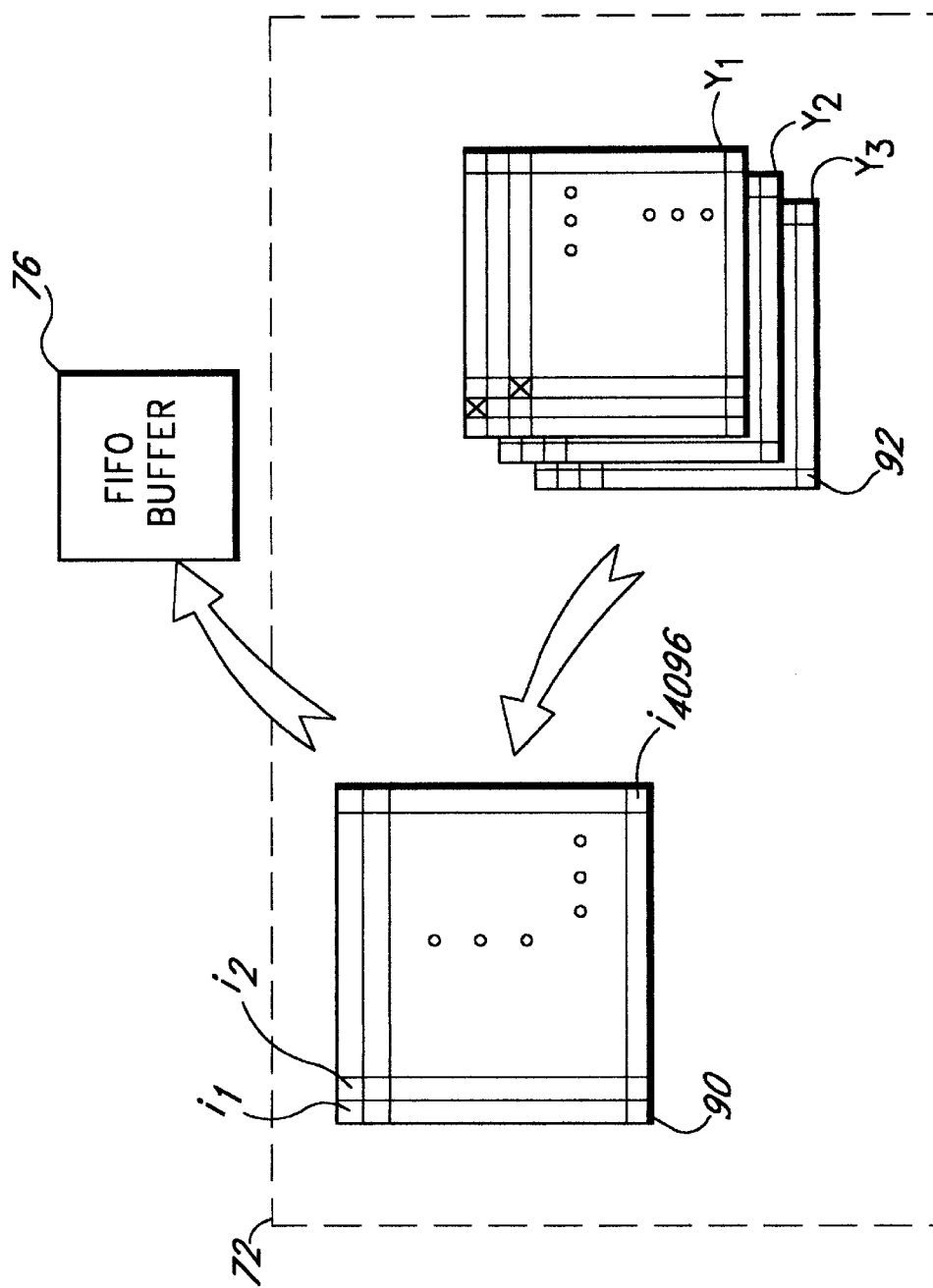
FIG. 5 is a functional representation of the X and Y array structure used in conjunction with the analyzer of FIG. 4.

The present embodiment of the analyzer 60 utilizes a form of memory indirect addressing as further described herein. Referring now to FIG. 5, the logic gate 72 stores data associated with the incoming pulse stream within its internal memory array 90 ("X" array) based on the binary value of the data produced by the ADC 64. Each memory location is then "indexed" ($i_n$) or incremented upon receipt of additional data with the same address. In this way, the data stream is scaled using a minimum amount of memory space.

A secondary array 92 ("Y" array) located within the same or different physical memory is created based on the gamma energy values desired to be filtered. This secondary array is generated based on previous observations and analysis of energy spectra obtained from similar or identical test specimens. For example, if it is known that inelastic scattering associated with Aluminum (a non-degradable material) in the cable conduit produces spectral lines at a set of different gamma energies, these energies can be programmed into the Y array and filtered as the X array is read out of memory. The counting or scaling interval (i.e., number of "counts" obtained in order to produce a given spectrum) can be set to any value consistent with the memory resources of the logic array 72 (or external memory, if used).

It is further contemplated that the present invention may be configured to identify specific degradable materials or constituents thereof present in the test specimen through comparison of test data to a predetermined "signature" gamma spectrum associated with a given material and stored within the logic array 72 or other memory. In one embodiment, the logic array 72 is programmed to obtain signature gamma spectrum data from the host PC 80 or external memory array and difference the index value for each gamma energy bin. This produces a type of difference spectrum which can then be analyzed (either manually or via an algorithm within the host PC 80) to determine the level or quality of match between the observed spectrum and the signature spectrum.

A field programmable gate array (FPGA) or application-specific integrated circuit (ASIC) with embedded memory is chosen as the logic gate 72 since it may efficiently perform the relatively simple tasks necessary to index and filter the digital data as described above, and no significant external is needed in the present application. Alternatively, if more sophisticated processing of the data is required (such as Fourier transform or other operation requiring a MAC stage), a more capable integrated circuit (such as a DSP having an external memory interface and DMA) may be utilized.

Referring again to FIG. 4, a first stage FIFO (first-in, first-out) buffer 68 and associated buffer manager 70 are used in each detector channel 82 to allow asynchronous storage and retrieval of spectral data obtained from each detector. This architecture is utilized primarily to prevent data loss during data collection when using a comparatively high neutron flux, which produces a high gamma detection event rate. Crystal detectors generally saturate at count rates on the order of 1E05–1E06 cps, and may begin to suffer severe degradation of spectral resolution at lower count rates. Based on a neutron flux of 1E06 n/s-4 π, the gamma count rate for the present invention (each detector, including background) is calculated to be well below saturation and spectral degradation levels. However, backend signal processing as described herein may, under certain circumstances, act as a "bottleneck" to data output from the ADC 64 at very high ADC sampling rates. The sample rate (SR) of the ADC(s) 64 is set higher than the maximum anticipated event or data rate (DR) rate to prevent data loss. Use of a first stage buffer allows for the accumulation of data between the ADC output and logic gate 72, thereby permitting use of a lower MIPS processor or logic gate 72 or alternatively, use of a high MIPS device and much additional processing of each data pulse. Use of second stage buffer 76 allows for the accumulation of data between the logic gate output and the storage/display device (personal computer) 80.

Data output from the PHD 66 is input to the first stage FIFO buffer 68 under control of the buffer management module (BMM) 70. Each buffer 68 may be further equipped with a separate overflow buffer 69, the buffer manager 70 monitoring the level within each primary buffer 68 and allocating data as necessary to the overflow buffer(s) 69 to prevent data loss. Such arrangement may be embodied in separate physical devices, or incorporated within a single piece of silicon. A Texas Instruments SN74ACT series device is chosen for the FIFO buffer of the present embodiment, although a wide variety of devices may be used with equal success. The logic gate 72 provides the necessary control signals to the buffer manager via it's control port to read out data from the buffer(s) 68 for further processing by the gate 72.

Data output from the logic gate 72 is input to the second stage buffer 76 under control of the second stage buffer management module (BMM) 78. Again, the buffer(s) 76 may be provided with a separate overflow buffer 77, the buffer manager 78 monitoring the level within the primary buffer 76 and allocating data as necessary to the overflow buffer(s) in similar fashion to the first stage. The PC 80 provides the necessary control signals to the second stage buffer manager 78 to read out data from the buffer(s) 76 for further processing, storage, or display by the PC 80. A standard parallel data interface 89 or I/O adapter board of the type well known in the computer art is used to interface the analyzer 60 with the PC 80.

Degradation of Materials

For purposes of the present disclosure, the term "degradable" shall mean any material or object whose chemical or physical composition changes, in whole or in part, as a result of the application of one or more stressors. Stressors as used herein refers to any chemical, electrical, physical or other force or influence including, without limitation, heat (whether by conduction, convection, or radiation), nuclear and cosmic radiation, electrical potential or current, chemicals, oxygen and other gases, volatization, or any combination thereof.

The primary constituent atoms within most commercially available polymers include carbon, hydrogen, oxygen, nitrogen, sulfur, chlorine, and fluorine. For example, in electrical cable insulation and jacketing, materials such as Hypalon™ (CSPE, or-chlorosulfonated polyethylene), EPR (ethylene propylene rubber), PVC (polyvinyl chloride), Tefzel™ (ethylene tetraflouroethylene) and XLPE (crosslinked polyethylene) are quite common. In addition to the base polymers listed above, many materials contain a variety of other substances or compounds which perform various ancillary functions. For example, lamp black (carbon) is commonly added to polyethylene in order to increase its resistance to cracking and degradation due to ultraviolet radiation. Clay (or other similar material) is commonly used as filler, often comprising the majority component within electrical cable insulation/jacketing in order to reduce cost. Plasticizers are commonly added to polymer formulations (including most notably PVC and CSPE) to increase their pliability and resistance to fatigue cracking. A typical formulation of EPR might consist of EPDM (ethylene propylene diene monomer), parrafin wax, zinc salts and oxides, vinylsilane, diadduct of hexachlorocyclopentadiene, dicumyl peroxide, SRF black, and antimony oxide.

Many polymer formulations also contain additives specifically designed to reduce the flammability of the cable insulation/jacketing under certain conditions. These so-called "fire retardants" volatize to varying degrees under exposure to heat and radiation, and are emitted from the cable at a rate related at least in part to the temperature/radiation dose rate to which the material is exposed. In many materials, the volatization of fire retardants roughly parallels the volatization of other flammable compounds; hence, the overall flammability of the material remains roughly constant as a function of thermal and/or radiation aging. However, as the fire retardants and flammable compounds are removed from the material, the relative concentration of the constituent atoms of these substances within the material as a whole change.

Similar to fire-retardants discussed above, plasticizers used in various polymer formulations are lost from the material as a function of aging and stressor application. Plasticizers are lost via both volatization and scission of the molecule. Plasticizer content has been shown to have a good correlation with, inter alia, elongation-at-break of certain materials in the early stages of component aging. Later in life, however, plasticizer content remains essentially constant for many materials, thereby limiting the effectiveness of these compounds as aging indicators during this period.

Ozone ($O_3$) is another stressor which may act on certain materials. Ozone is generated in the air as a result of the interaction of ionizing radiation with monatomic or diatomic oxygen, or by corona discharge ionization. Similar to oxygen diffusion. ozone effects occur predominately at the surface of the object where the ozone concentration is highest. Generally, however, most modern polymer formulations are resistant to the effects of ozone.

Cable components may also be exposed to chemical by-products of the thermal or radiolytic decomposition of cable jacketing, insulation, fire-resistant coatings, or other organic components. Many materials commonly used in cable construction either contain or are manufactured using potentially corrosive chemicals such as chlorides, peroxides, or sulfurous compounds. Chemical by-products originating from decomposition of cable components may result in several degradation mechanisms, including softening, swelling, or decomposition of other organics within the cable structure. Plasticizer migration (PVC) can also result in swelling of adjacent elastomers.

For example, neoprene rubber (chloroprene), PVC (polyvinyl chloride), CSPE (chlorosulfonated polyethylene), and CPE (chloropolyethylene) may all produce chlorine ions (and hydrochloric acid) upon decomposition. Additionally, elastomers including EPR/EPDM are cured using peroxide or sulfur compounds that can be leached from the material as it ages or is subjected to certain environmental conditions (such as heat or wetting). Copolymers such as ethylene vinyl acetate (semiconducting shield material) may also decompose to produce by-products such as weak acids.

Degradation resulting from copper-catalyzed oxidation reactions may occur in certain polymers as well. A catalyst is defined as a substance that affects the rate or the direction of a chemical reaction, but is not appreciably consumed in the process. Because of its proximity to the insulation, ions from copper-based conductors may act as catalysts for oxidation reactions within the insulation, thereby accelerating its degradation. This will occur primarily in areas where the insulation is in direct contact with the conductor.

By-products are also generated from chemically crosslinked XLPE as a result of the high temperature/pressure curing process. By-products such as acetophenone, cumene, and alpha methyl styrene are produced as the chemical crosslinking agent (dicumyl peroxide) decomposes.

Another potential aging mechanism is hydrolytic degradation of mylar (polyethylene terephthalate) shield film under exposure to high temperature and moisture. Under this mechanism, water increasingly reacts with the mylar polymer as temperature is increased.

Figure 6:
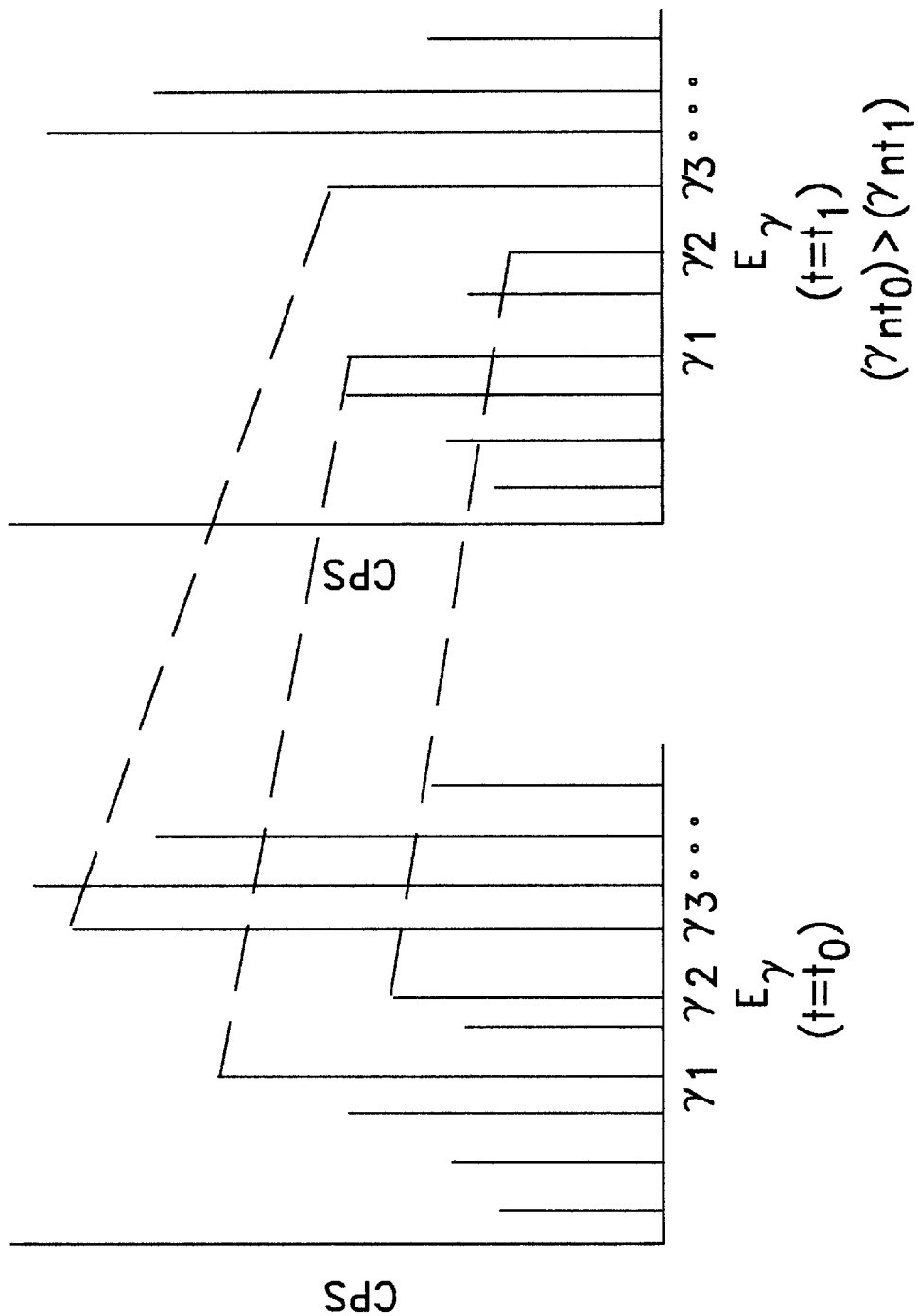
FIGS. 6a and 6b illustrate two typical gamma spectra obtained from an in-situ specimen at successive aging intervals.

In sum, there are a substantial number of different possible aging mechanisms for electrical cable components (and more broadly, degradable components), each of which may ultimately vary the concentration of various atomic species within the material. The effects of these aging mechanisms are specific to each class or even formulation of material, and hence generally must be analyzed individually. For example, as discussed above, it can be shown for some materials that the rate of fire retardant loss is roughly proportional to the thermal aging applied to the material (at least for certain aging intervals). Hence, the signature gamma lines associated with the specific fire retardant present in that material are used as an indirect indicator of thermal aging. Since fire retardant volatizes, the atomic concentration and hence inelastic scattering of neutrons by the constituent atoms (which may include carbon, hydrogen, bromine, fluorine, or chlorine) will also vary as a function of aging. As the atomic concentration (N) of a given element is reduced, the associated gamma yield at specific energies is reduced as well (assuming a measurable gamma yield for the incident neutron energy selected). Hence, a reduction in atomic concentration due to aging stressors is ultimately reflected as a reduction in detected counts at those energies as compared to prior spectra of the same sample; see FIGS. 6a and 6b, which show typical gamma spectra taken from the same specimen at two different levels of aging. The following generalized formula represents the approximate gamma counting rate for a given material, gamma energy, and neutron energy in the apparatus of the present invention (assuming no detector or processing circuit saturation):

$$CR = S \cdot d\phi \cdot E_d \cdot \gamma_i \cdot AF$$

Where:

CR=Counting Rate (cps)

S=Total neutron source strength (neutrons/s-4 $\pi$)

$d\phi$=Uncollimated solid angle subtended by active detector area (steradians)

$E_d$=Detector efficiency at selected gamma energy $\gamma i$=Gamma yield for ith material for selected gamma energy and incident neutron energy AF=Attenuation factor for interposed materials for selected gamma energy Note that the gamma yield $\gamma_I$ as shown in the above relationship is a complex function of the inelastic scattering cross-section ($\sigma$) of the various constituent atoms, their atomic concentrations (N), and the incident neutron energy. Obviously, the yield at different gamma energies will vary for each material.

The present invention further contemplates the evaluation of multiple degradation processes during the installed lifetime of the degradable component as required. For example, while changes in the gamma spectrum associated with plasticizer loss may be useful during the earlier stages of component life, fire retardant volatization may be a better indicator of component condition later in life.

Neutron and Gamma Attenuation in Surrounding Materials

One of the principal benefits of the present invention is its ability to "look through" most any components or materials interposed between the test subject 11 and neutron source 12. This unique property results from the use of energetic neutrons which have a very low scattering/absorption cross-section in most materials of relatively low thickness (i.e., less than a few inches). Obviously, some attenuation of the incident neutron beam will occur. Unlike the interaction of gamma rays with matter (described below), the energy and spatial distribution of incident neutrons will vary as a function of the attenuating material. Specifically, a fraction of the neutrons in the incident beam 13 will be reduced in energy, and a fraction will be scattered at angles relative to the beam centerline. This characteristic is due not to coulombic interaction, but rather the inelastic scattering of the comparatively massive neutron with other particles in a given nucleus. The neutron spatial and energy distributions after passage through an intervening material are not critical in the present embodiment of the invention, since 1) a sufficient population of sufficiently energetic neutrons will exist after passing through most any material in most contemplated applications; 2) gamma rays (and not neutrons) are detected upon their egress from the test subject; and 3) the spatial position of the test subject is not being measured, hence, any errors induced by alteration of the spatial distribution of neutrons will only affect the scope of material within the test subject 11 which is analyzed. This affords the invention the ability to analyze test subjects shielded behind any number of types and configurations of materials. The aforementioned secondary gamma emissions are prompt (occur on the order of femtoseconds after scattering) and spatially distributed around the target atom (s).

Unlike neutrons, gamma rays (photons) generally retain their initial energy regardless of intervening material; rather, such materials act to attenuate the gamma flux, yet not alter the spectral or spatial distribution. Lower energy gammas are attenuated much more severely by relatively thin materials than are higher energy gammas. For example, the attenuation of 100 KeV gamma flux in 1 inch of steel is almost complete, whereas the attenuation of a 10 MeV gamma flux in the same material is fairly minimal. A common measure of this property is so-called "tenth thickness", defined as the thickness of a given material required to attenuate an incident gamma flux of a given energy to one-tenth of it's initial value.

Damage to the test subject 11 and any intervening material resulting from incident neutron radiation during testing with the apparatus 10 described herein is not considered significant, since the total integrated dose (TID) applied to a given test specimen even over several in-situ tests is well below the threshold dose necessary to result in measurable property changes in the target. Most elastomers thermoplastics, and thermosets have estimated neutron threshold doses on the order of 1E14 n/cm2, whereas the neutron dose imparted during a standard testing protocol of the present invention is several orders of magnitude below this value. Even when accounting for differences in neutron energy, the dose to a given component resulting from even frequent periodic testing during its lifetime is well below the threshold value cited above. Furthermore, with certain test components (such as cable), slightly different physical locations on the cable with essentially identical environmental conditions may be used for subsequent tests in order to distribute the neutron/gammadose within the component. A tightly collimated neutron beam (given the same flux emitted from the source 12 prior to collimation by the collimator 14) allows greater spatial control, yet generally at the expense of slower counting rates and longer integration times.

Aging Analysis and Method

As is presently known in the art, specimens of similar or identical construction to the in-situ components to be analyzed may be aged in a controlled fashion in order to observe changes in various physical, chemical, electrical, or atomic characteristics. Typically, the aging is accelerated in nature (in order to make the results available more immediately), and attempts to replicate the environmental conditions to which the component will be exposed as closely as possible. These laboratory or artificially aged specimens are then used as "yardsticks" against which in-situ components are compared in order to evaluate the condition (level of aging) of the component.

Figure 7:
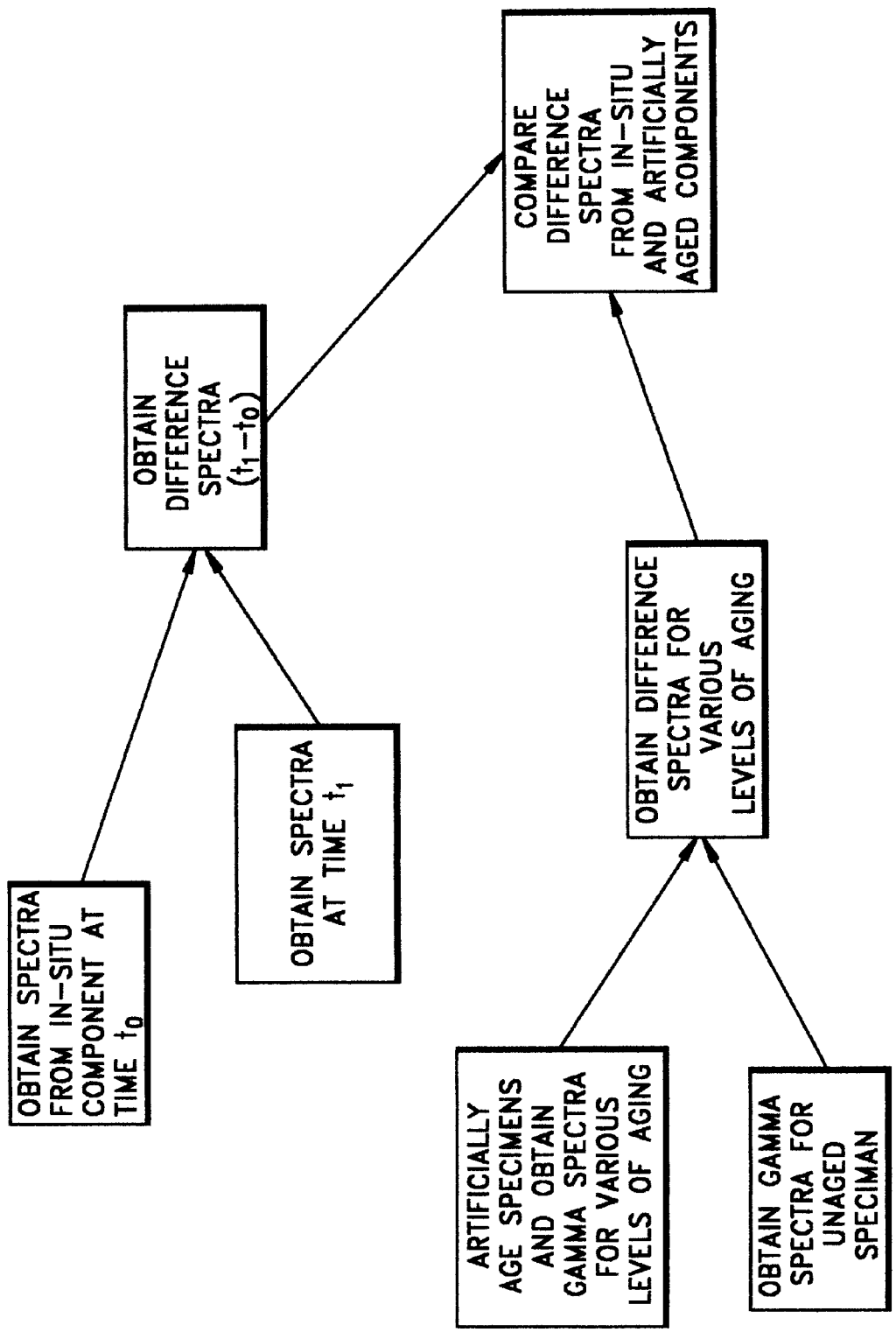
FIG. 7 is a functional flow chart illustrating one embodiment of the aging estimation method of the present invention.

The present invention utilizes the foregoing general approach to evaluate in-situ specimens as depicted in FIG. 7. First, a specimen similar or identical to the in situ component being evaluated is aged, either naturally or artificially, in a manner consistent with the natural aging of the in-situ component. For example, if the in-situ component is exposed to heat and radiation, similar aging is applied to the specimen to induce similar types of degradation. The specimen is aged to or beyond the maximum expected level of aging anticipated for the in-situ component to provide a complete aging profile. The techniques used to artificially and naturally age specimens for purposes of in-situ component aging analysis are well known and understood in the art, and accordingly need not be explained further herein. At selected intervals during the specimen aging process, gamma spectra are obtained from the specimen using the above-described apparatus and stored within the memory of the analyzer 60 or host PC 80 for later use. For example, the spectra (or sets of spectra) may be obtained at 25, 50, 75, and 100% of anticipated aging of the specimen. The spectra are also analyzed to identify gamma energies associated with non-degradable components within the specimen, such as the copper conductors of the cable. These gamma energies are recorded for later use with the pulse height discrimination/filterfunctions of the analyzer 60 previously described. It should be noted that essentially the entire gamma spectrum obtained from the specimen is used in the analysis, since as previously described, different spectral lines may be more or less useful as a function of the level of aging.

Next, the apparatus of the present invention is again used to obtain a first spectrum (or set of spectra if averaging or more complex statistical analysis is used) of the in-situ component at a given time in the lifetime of that component. In the case of intervening materials such as conduit or valve bodies, the representative spectra obtained from the insitu component is differenced, using the analyzer 60 described above, from that of the laboratory aged specimen for a comparable level of aging in order to identify the spectral lines associated with the intervening material. The choice of specimen spectrum for comparison to that obtained from the in-situ component is not critical (so long as a spectrum representing a roughly comparable level of aging is chosen), since variations in the aging of the degradable materials will be minimal in comparison to the more salient differences relating to the non-degradable materials. The gamma energies associated with these "salient" differences are then entered into the filtering algorithm (i.e., the "Y" array values) to permit filtering of subsequent spectra obtained with the intervening material in place. Note that multiple arrays (filter values) may be stored in memory and accessed as desired depending on the specific application.

Lastly, a second spectrum (or set of spectra) is obtained from the in-situ specimen at a later time in life, or after the application of a significant stressor. This second spectrum is then filtered as necessary and compared to the first spectrum in order to identify changes in the material as a function of aging/stressor application. Specifically, the differences between the first and second spectra from the in-situ specimen are compared to the difference between the gamma spectrum for the unaged laboratory specimen and those taken at subsequent times during the artificial (or natural) aging regimen as shown in FIG. 8. For example, if the difference spectrum for the in-situ specimen indicates a change of 1000 cps for a gamma energy of 3 MeV, and the 25% and 50% aging spectra for the laboratory specimen indicate changes at 3 MeV of 500 cps and 2000 cps, respectively, the aging of the in-situ component can be inferred to be between 25% and 50%. Obviously, more sophisticated differencing and analytical interpolation techniques may be employed to more precisely estimate the level of aging of the component; the foregoing example is merely illustrative of the general methodology of the present embodiment. Note also that such comparisons may be functionally implemented entirely in software operating on the PC processor 80, such software being easily produced using techniques well known in the computer arts.

It should be recognized that while the foregoing discussion has described a specific sequence of steps necessary to perform the method of the present invention, other sequences (such as obtaining the in-situ measurements prior to conducting artificial aging of the laboratory specimens) of steps may be used depending on the particular application.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of estimating the condition of a degradable object, comprising:

irradiating at least a portion of said object with neutrons;

detecting, at a first time, secondary radiation emissions from said object resulting from said irradiation;

generating a first radiation spectrum based on said detected secondary radiation emissions;

comparing said first radiation spectrum to a second radiation spectrum obtained by irradiating said object at a second time; and comparing differences in said first and second radiation spectra to those obtained from a laboratory or naturally aged specimen in order to estimate the condition of said degradable object.

2. The method of claim 1, wherein said degradable object comprises an electrical cable.

3. The method of claim 1, further comprising applying at least one stressor to said degradable object between said first and second times.

4. A method of estimating the condition of an electrical cable, comprising:

irradiating at least a portion of said cable with neutrons;

detecting secondary radiation emitted from said cable resulting from said act of irradiating;

generating a radiation spectrum based on said secondary radiation emissions; and analyzing said spectrum to estimate the condition of said cable.

5. The method of claim 4, further comprising applying at least one stressor to said cable to induce changes in said radiation spectrum.

6. The method of claim 4, wherein said electrical cable is contained at least partially within a conduit.

7. A method of estimating the condition of a polymer seal, comprising:

irradiating at least a portion of said polymer with neutrons;

detecting secondary radiation emitted from said seal resulting from said act of irradiating;

generating a radiation spectrum based on said secondary radiation emissions; and analyzing said spectrum to estimate the condition of said polymer seal.

8. The method of claim 7, wherein the act of analyzing comprises comparing said radiation spectrum to another radiation spectrum obtained by irradiating said polymer seal at a different point in time.

* * * * *